United States Patent [19]

Coveney et al.

[11] Patent Number: 4,940,695

[45] Date of Patent: Jul. 10, 1990

[54] BISMUTH-CONTAINING PHARMACEUTICAL COMPOSITIONS

[75] Inventors: Leila D. Coveney, Cincinnati, Ohio; Linda C. Jones, Aurora, Ind.; Jerry R. Maney, Mason, Ohio

[73] Assignee: The Procter & Gamble Company, Cincinnati, Ohio

[21] Appl. No.: 130,760

[22] Filed: Dec. 10, 1987

[51] Int. Cl.$^5$ .................. A61K 31/715; A61K 31/60; A61K 31/29

[52] U.S. Cl. ..................... 514/57; 514/503; 514/925; 514/159

[58] Field of Search ............. 514/57, 503, 925, 159

[56] References Cited

U.S. PATENT DOCUMENTS 4,801,454  1/1989  Coveney et al. ............ 514/503

FOREIGN PATENT DOCUMENTS 217440  4/1987  European Pat. Off.

OTHER PUBLICATIONS

Handbook of Nonprescription Drugs, 8th Edition (American Pharmaceutical Association, Washington, D.C.; 1986); pp. 73–74.

Primary Examiner—Ronald W. Griffin
Assistant Examiner—Everett White
Attorney, Agent, or Firm—Kim William Zerby; Douglas C. Mohl; Richard C. Witte

[57] ABSTRACT

Pharmaceutical compositions suitable for oral administration comprising: (a) pharmaceutically-acceptable bismuth-containing agents such as bismuth subsalicylate; (b) pharmaceutically-acceptable non-ionic cellulose ether polymers such as methylcellulose; and (c) magnesium aluminum silicate. The ratio of bismuth to non-ionic cellulose ether polymer is greater than about 1.5:1. Compositions in the form of liquids containing water are preferred.

This invention also relates to methods for treating or preventing disturbances of the gastrointestinal tract in humans or lower animals by orally administering a composition of the present invention.

23 Claims, No Drawings

BISMUTH-CONTAINING PHARMACEUTICAL COMPOSITIONS

BACKGROUND OF THE INVENTION

The present invention relates to bismuth-containing pharmaceutical compositions suitable for oral administration to humans or lower animals. This invention also relates to methods for treating or preventing disturbances of the gastrointestinal tract by administering a composition of the present invention.

Bismuth-containing pharmaceutical compositions are well known, being used widely to treat a variety of gastrointestinal disorders such as nausea, heartburn, and diarrhea. One such product is liquid Pepto-Bismol (sold by The Procter & Gamble Company). This product contains bismuth/subsalicylate and a methylcellulose/magnesium aluminum silicate suspension system. Another is Pabizol with Paregoric (sold by Rexall) which is a liquid suspension said to contain, in addition to opium, bismuth subsalicylate (17.0 mg/ml), aluminum magnesium silicate (8.83 mg/ml), and hydroxypropylmethylcellulose (6.7 mg/ml). These and other bismuth-containing compositions are described generally in "Handbook of Nonprescription Drugs, 8th Edition" (American Pharmaceutical Association, Washington, D.C.; 1986), pages 73-74, the disclosures of which are incorporated herein by reference in their entirety.

Notwithstanding the great effort already put forth to identify bismuth-containing compositions, there remains a continuing need to identify new compositions which have improved pharmaceutical properties. The bismuth-containing pharmaceutical compositions of the present invention have such improved properties, including being surprisingly more effective for coating the gastrointestinal tract.

Thus, an object of the present invention is to provide bismuth-containing pharmaceutical compositions which are effective for coating the gastrointestinal tract. Another object is to provide compositions suitable for oral administration which are effective for treating or preventing disturbances of the gastrointestinal tract. An object of the present invention is also to provide bismuth-containing compositions effective for delivering higher doses of bismuth-containing agents to the gastrointestinal tract. A further object is to provide pharmaceutical compositions containing bismuth-containing agents having enhanced efficacy. Finally, an object is to provide methods for treating or preventing disturbances of the gastrointestinal tract in humans or lower animals.

These and other objects of the present invention will become readily apparent from the detailed description which follows.

All percentages and ratios used herein are by weight unless otherwise specified.

SUMMARY OF THE INVENTION

The present invention relates to pharmaceutical compositions suitable for oral administration, especially those which are particularly effective for delivering bismuth-containing agents to the gastrointestinal tract by having improved coating action. These compositions comprise from about 0.1% to about 50% of a pharmaceutically-acceptable bismuth-containing agent, from about 0.1% to about 25% of a pharmaceutically-acceptable non-ionic cellulose ether polymer, and from about 0.1% to about 25% of magnesium aluminum silicate. Furthermore, the compositions are formulated such that the ratio of bismuth to the non-ionic cellulose ether polymer is greater than about 1.5:1. Particularly preferred are liquid compositions which comprise from about 75% to about 99% of water.

The present invention further relates to methods for treating or preventing disturbances of the gastrointestinal tract (e.g., diarrhea, gastritis, ulcers). These methods comprise orally administering to a human or lower animal in need of such treatment or prevention a safe and effective amount of a pharmaceutical composition of the present invention.

DETAILED DESCRIPTION OF THE INVENTION

Pharmaceutical Compositions

The pharmaceutical compositions of the present invention comprise the following essential components:

(a) pharmaceutically-acceptable bismuth-containing agent;

(b) pharmaceutically-acceptable non-ionic cellulose ether polymer; and (c) magnesium aluminum silicate.

These components, and the weight percentages and specific relative ratios for these components, are described in detail hereinafter.

The term "pharmaceutically-acceptable", as used herein, means that the components present in the compositions of the present invention are compatible and suitable for oral administration to a human or lower animal. The term "compatible", as used herein, means that the components of the pharmaceutical compositions are capable of being commingled with each other in a manner such that there is no interaction which would substantially reduce the pharmaceutical efficacy of the pharmaceutical compositions under ordinary use situations. Pharmaceutically-acceptable components for use herein must, of course, be of sufficiently high purity and sufficiently low toxicity to render them suitable for oral administration to the human or lower animal being treated.

(a) Pharmaceutically-Acceptable Bismuth-Containing Agents

The pharmaceutical compositions of the present invention essentially comprise a bismuth-containing agent, preferably in the form of a pharmaceutically-acceptable salt. Such bismuth-containing agents include, for example, bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention. More preferred are bismuth subcitrate, bismuth subsalicylate, and mixtures thereof. Bismuth subsalicylate is most preferred.

These agents are well known in the art, and are commercially available. Their formulation and use in commercial compositions are also well-known, being sold, for example, as DeNol (bismuth subcitrate; sold by Gist-Brocades, N.V.), Noralac (containing bismuth aluminate, alginic acid, and magnesium carbonate; manufactured by North American Pharmaceuticals), Roter bismuth (containing bismuth subnitrate; sold by Roter Laboratories), Fensobar Polvo; (containing bismuth subcarbonate among other materials; manufactured by USV Pharmaceutical Corporation), and Pepto-Bismol (containing bismuth subsalicylate; sold by The Procter & Gamble Company).

The pharmaceutical compositions of the present invention typically comprise, by weight, from about 0.1 to about 50% of a bismuth-containing agent, preferably from about 1% to about 20%, more preferably from about 1% to about 5%, and most preferably from about 3% to about 4%.

(b) Pharmaceutically-Acceptable Non-ionic Cellulose Ether Polymers

The pharmaceutical compositions of the present invention essentially comprise a pharmaceutically-acceptable non-ionic cellulose ether polymer. Preferred are non-ionic cellulose ether polymers selected from alkylcelluloses (e.g., methylcellulose), hydroxyalkylalkylcelluloses (e.g., hydrocypropylmethylcellulose; hydroxybutylmethylcellulose; hydroxyethylmethylcellulose; ethylhydroxyethylcellulose), hydroxyalkylcelluloses (e.g., hydroxyethylcellulose; hydroxypropylcellulose), and mixtures thereof. Most preferred are alkylcelluloses, especially methylcellulose. Pharmaceutically-acceptable non-ionic cellulose ether polymers are well known in the art, and are described in more detail in "Handbook of Water-Soluble Gums and Resins" (McGraw-Hill Book Company, New York; 1980; Davidson, editor), chapters 3, 12, and 13, the disclosures of which are incorporated herein by reference in their entirety.

Representative examples of pharmaceutically-acceptable non-ionic cellulose ether polymers useful in the compositions of the present invention are: Methocel A ® (methylcellulose, sold by The Dow Chemical Company); Metolose SM ® (methylcellulose, sold by Shin Etsu Chemical Products Ltd.); and Methocel E ® (hydroxypropylmethylcellulose, sold by The Dow Chemical Company).

The pharmaceutical compositions of the present invention typically comprise, by weight, from about 0.1% to about 25% of a non-ionic cellulose ether polymer, preferably from about 0.1% to about 10%, more preferably from about 0.5% to about 3%, and most preferably from about 0.5% to about 1.5%.

(c) Magnesium Aluminum Silicate

The pharmaceutical compositions of the present invention further essentially comprise a magnesium aluminum silicate. Magnesium aluminum silicate (or aluminum magnesium silicate) is of the formula $Al_2MgO_8Si_2$, occurring naturally in such smectite minerals as colerainite, saponite, and sapphirine. Refined magnesium aluminum silicates useful herein are readily available, such as Veegum, magnesium aluminum silicate, manufactured by R. T. Vanderbilt Company, Inc.

The pharmaceutical compositions of the present invention typically comprise, by weight, from about 0.1% to about 25% of a magnesium aluminum silicate, preferably from about 0.1% to about 10%, more preferably from about 0.1% to about 5%, and most preferably from about 0.5% to about 1.5%.

(d) Optional Components

In addition to the essential components described hereinbefore, the pharmaceutical compositions of the present invention may comprise additional optional components selected as appropriate for the particular orally-administrable dosage form being used. Various oral dosage forms can be used, including such solid forms as tablets, capsules, granules and bulk powders, as well as the preferred aqueous liquid forms. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents.

Liquid oral dosage forms are preferred herein. Compositions herein in the form of a liquid include, for example, aqueous solutions, emulsions, suspensions, solutions and/or suspensions reconstituted from non-effervescent granules and effervescent preparations reconstituted from effervescent granules. They may contain suitable solvents, preservatives, emulsifying agents, suspending agents, diluents, sweeteners, melting agents, coloring agents, and/or flavoring agents. Preferably, these liquid dosage forms comprise water, typically at a level by weight of from about 75% to about 99%, preferably from about 85% to about 98%, and most preferably from about 92% to about 96%.

Some examples of substances which can serve as pharmaceutically-acceptable optional components are sugars such as lactose, glucose and sucrose; starches such as corn starch and potato starch; powdered tragacanth; malt; gelatin; talc; stearic acid; magnesium stearate; calcium sulfate; and polyols such as propylene glycol, glycerine, sorbitol, mannitol, and polyethylene glycol. Wetting agents and lubricants such as sodium lauryl sulfate, as well as coloring agents, flavoring agents, excipients, tableting agents, stabilizers, anti-oxidants, and preservatives can also be present. Other compatible pharmaceutical additives and actives (e.g., NSAI drugs; $H_2$ receptor blocking anti-secretory agents) may be included in the pharmaceutically-acceptable optional components for use in the compositions of the present invention.

The choice of pharmaceutically-acceptable optional components to be used in the compositions of the present invention is basically determined by the form and aesthetic properties desired for the composition. Pharmaceutically-acceptable optional components suitable for the preparation of compositions herein for oral administration are well known in the art. Their selection will depend on secondary considerations like taste, cost, and shelf stability, which are not critical for the purposes of the present invention, and can be made without difficulty by a person skilled in the art.

(e) Ratio of Essential Components

The use of some of the hereinbefore described essential components together in pharmaceutical compositions is obviously not new, since, for example, compositions such as regular strength, Pepto-Bismol (containing 1.75% bismuth subsalicylate, about 1% methylcellulose and about 1% Veegum; sold by The Procter & Gamgle Company) has been sold for years containing these same components. What is new, and especially surprising, is that by selecting a non-ionic cellulose ether material as part of the suspension agent and increasing the ratio of bismuth to this suspending agent, there is an unexpected improvement in the coating action produced by these compositions. Thus, there is an unexpected improvement in the delivery of the bismuth agent to the walls of the gastrointestinal tract. This improved coating action is not only beneficial in and of itself for prophylactic purposes, but also should provide additional benefits for the treatment of diseases such as ulcers and gastritis (especially those involving *Campylobacter pylori* infection).

This unexpected coating benefit has been observed by measuring levels of bismuth on the gastric mucosa through use of endoscopy/biopsy procedures. (Methods for determining the coating action of bismuth compositions and/or compounds are known, being described, for example, in Goldenberg et al., "Protective Effect of Pepto-Bismol Liquid on the Gastric Mucosa of Rats", *Gastroenterology*, 69(3), pp. 636-640 (1975); Koo et al., "Selective Coating of Gastric Ulcer by Tripotassium Dicitrato Bismuthate in the Rat", *Gastroenterology*, 82, pp. 864-870 (1982); Salmon et al., "Evaluation of colloidal bismuth (De-Nol) in the treatment of duodenal ulcer employing endoscopic selection and follow up", Gut, 15, pp. 189-193 (1974); and "Analysis of Bismuth in Blood and Urine by Anodic Stripping Voltammetry", available from ESA Laboratories, Inc.; the disclosures of all these publications being incorporated herein by reference in their entirety).

For example, a composition of the present invention formulated as described hereinafter in Example 1 (having 3.5% bismuth subsalicylate and a ratio of bismuth to methylcellulose of 1.87:1) has two times as much bismuthsubsalicylate in the formulation as regular strength Pepto-Bismol (having 1.75% bismuth subsalicylate, and a methylcellulose/Veegum suspension system at the same concentrations as the Example 1 composition; bismuth to methylcellulose ratio of 0.93:1). However, rather than observing the expected two-fold increase in coating by the composition of the present invention, this composition demonstrates a surprising three-fold increase in coating (i.e., approximately 100% greater than expected coating benefit). If essentially the same formulation as Example 1 is prepared using xanthan gum in place of methylcellulose as part of the suspension system (similar to the xanthan gum/Veegum suspension system described in European Patent Application Publication No. 217,440, published Apr. 8, 1987), only the expected two-fold increase in coating by the bismuth subsalicylate is observed.

Therefore, for purposes of the present invention, the ratio of bismuth to non-ionic cellulose ether polymer is greater than about 1.5:1, preferably within the range of from about 1.5:1 to about 9:1, more preferably from about 1.5:1 to about 3:1, and most preferably from about 1.5:1 to about 2.5:1. For purposes of providing a uniform standard for the amount of bismuth-containing agent to be utilized in the compositions of the present invention, the ratios herein refer to the weight of elemental bismuth present in the compositions relative to the weight of the non-ionic cellulose ether polymer. For example, the weight percent of bismuth in a composition containing 3.5% bismuth subsalicylate is 2.02%; and the ratio of bismuth to methylcellulose in such a composition containing 1.079% methylcellulose is 1.87:1 (the ratio of bismuth subsalicylate to methylcellulose in such a composition is 3.24:1). Finally, for the compositions herein, it is further preferred that the ratio of bismuth to the total combined weight of non-ionic cellulose ether polymer/magnesium aluminum silicate suspension system be within the range of from about 0.1:1 to about 10:1, preferably from about 0.1:1 to about 5:1, and more preferably from about 0.5:1 to about 1.5:1.

Methods For Treating Or Preventing Disturbances Of The Gastrointestinal Tract Another aspect of the present invention is methods for treating or preventing disturbances of the gastrointestinal tract. Such methods comprised orally administering, to a human or lower animal in need of such treatment or prevention, a safe and effective amount of a pharmaceutical composition of the present invention.

The term "disturbances of the gastrointestinal tract", as used herein, encompasses any disease or other disorder of the gastrointestinal tract which is treatable or preventable by oral administration of bismuth-containing agents. Such disturbances are well known in the art, and include, for example: nausea; diarrhea, including the prevention of "travelers diarrhea" (as described, for example, in DuPont et al., "Prevention of Travelers' Diarrhea by the Tablet Formulation of Bismuth Subsalicylate", *JAMA*, 257, pages 1347-1350 (1987), the disclosures of which are incorporated herein by reference in their entirety); heartburn; indigestion; upset stomach; and the treatment or prevention of gastritis and ulcers, especially when *Campylobacter pylori* infection is present (as described, for example, in European Patent Application Publication Numbers 206,626 and 206,627, published Dec. 30, 1986, by Marshall; and in McNulty et al., "Successful Therapy of *Campylobacter Pyloridis* Gastritis", *Gastroenterology*, 90, page 1547 (1986), all being incorporated herein by reference in their entirety).

The phrase "safe and effective amount", as used herein, means an amount of a composition according to the present invention high enough to significantly and positively modify the condition to be treated or prevented, but low enough to avoid serious side effects (at a reasonable benefit/risk ratio), within the scope of sound medical judgement. The safe and effective amount of the composition will vary with the particular condition being treated, the age and physical condition of the patient being treated, the severity of the condition, the duration of treatment, the nature of concurrent therapy, the specific agent employed, the particular dose form utilized, and like factors within the knowledge and expertise of the attending physician.

The methods of the present invention typically involve administering the compositions in an amount sufficient to deliver from about 10 milligrams to about 5000 milligrams of bismuth per day. (Again, as noted hereinbefore, the quantity of bismuth-containing agent being administered by the present methods is standardized by way of indicating the elemental bismuth present in the composition). Preferably, from about 100 milligrams to about 3000 milligrams of bismuth is administered per day. On a per dose basis, preferred is from about 10 milligrams to about 1000 milligrams of bismuth per dose.

Preferably, the bismuth-containing agent used for the methods herein is bismuth subcitrate and, especially, bismuth subsalicylate. If bismuth subsalicylate is utilized, the preferred daily dose of bismuth subsalicylate is within the range of from about 100 milligrams of bismuth subsalicylate to about 8500 milligrams of bismuth subsalicylate, and more preferably from about 1000 milligrams to about 6000 milligrams. Preferred individual doses of bismuth subsalicylate are from about 100 milligrams to about 2000 milligrams, with from about 250 milligrams to about 1500 milligrams being most preferred.

The following example further describes and demonstrates an embodiment within the scope of the present invention. This example is given solely for the purpose of illustration, and is not to be construed as a limitation of the present invention since many variations thereof are possible without departing from its spirit and scope.

EXAMPLE 1

Liquid Pharmaceutical Composition

A composition of the present invention in liquid form suitable for oral administration is prepared using conventional methods and having the following components.

| Components | Weight % |
| --- | --- |
| Veegum[1] | 0.985 |
| Methylcellulose[2] | 1.079 |
| Bismuth subsalicylate | 3.50 |
| FD&C red #3 | 0.0364 |
| FD&C red #40 | 0.00539 |
| Sodium saccharin | 0.06081 |
| Sodium salicylate | 0.05983 |
| Salicylic acid | 0.07062 |
| Methyl salicylate | 0.060 |
| Peppermint oil | 0.005 |
| Purified water | Q.S. |

[1]Magnesium aluminum silicate manufactured by R. T. Vanderbilt Company, Inc.
[2]Methocel A ®, supplied by The Dow Chemical Company.

This composition may be prepared by first mixing the Veegum in chilled water, and then adding to this mixture a warm aqueous slurry of methylcellulose followed by FD&C red #3, bismuth subsalicylate slurry, FD&C red #40, sodium saccharin, sodium salicylate, peppermint oil, and a slurry of salicylic acid and methyl salicylate. Finally, sufficient water is added to dilute the composition to the desired final weight, and the composition is mixed to homogeneity.

Ingestion of 2 tablespoonfuls (approximately 30 ml containing about 1050 mg of bismuth subsalicylate) of this liquid four times per day is effective for treating diarrhea, heartburn, and nausea. Similarly, an effective composition may also be prepared and orally administered by using bismuth subcitrate in place of the bismuth subsalicylate in the above formulation at the same bismuth to methylcellulose ratio.

What is claimed is:

1. Pharmaceutical compositions for oral administration comprising:
    (a) from about 0.1% to about 50% of at least one pharmaceutically-acceptable bismuth-containing agent;
    (b) from about 0.1% to about 25% of at least one pharmaceutically-acceptable non-ionic cellulose ether polymer; and
    (c) from about 0.1% to about 25% of magnesium aluminum silicate;
  and wherein further the ratio of bismuth to non-ionic cellulose ether polymer is greater than about 1.5:1.

2. Pharmaceutical compositions according to claim 1 wherein the ratio of bismuth to non-ionic cellulose ether polymer is within the range of from about 1.5:1 to about 9:1.

3. Pharmaceutical compositions according to claim 2 comprising:
    (a) from about 1% to about 20% of at least one pharmaceutically-acceptable bismuth-containing agent;
    (b) from about 0.1% to about 10% of at least one pharmaceutically-acceptable non-ionic cellulose ether polymer; and
    (c) from about 0.1% to about 10% of magnesium aluminum silicate.

4. Pharmaceutical compositions according to claim 3 wherein:
    (a) the pharmaceutically-acceptable bismuth-containing agent is selected from the group consisting of bismuth citrate, bismuth subcitrate, tripotassium dicitrato bismuthate, bismuth tartrate, bismuth subsalicylate, and mixtures thereof; and
    (b) the pharmaceutically-acceptable non-ionic cellulose ether polymer is selected from the group consisting of alkylcelluloses, hydroxyalkylalkylcelluloses, hydroxyalkylcelluloses, and mixtures thereof.

5. Pharmaceutical compositions according to claim 4 wherein:
    (a) the pharmaceutically-acceptable bismuth-containing agent is selected from bismuth subcitrate, bismuth subsalicylate, and mixtures thereof; and
    (b) the pharmaceutically-acceptable non-ionic cellulose ether polymer is an alkylcellulose.

6. Pharmaceutical compositions according to claim 3 in the form of a liquid comprising:
    (a) from about 1% to about 5% of at least one pharmaceutically-acceptable bismuth-containing agent;
    (b) from about 0.5% to about 3% of at least one pharmaceutically-acceptable non-ionic cellulose ether polymer;
    (c) from about 0.1% to about 5% of magnesium aluminum silicate; and
    (d) from about 85% to about 98% of water;
  and wherein further the ratio of bismuth to non-ionic cellullse ether polymer is within the range of from about 1.5:1 to about 3:1.

7. Pharmaceutical compositions according to claim 6 wherein:
    (a) the pharmaceutically-acceptable bismuth-containing agent is selected from bismuth subcitrate, bismuth subsalicylate, and mixtures thereof; and
    (b) the pharmaceutically-acceptable non-ionic cellulose ether polymer is selected from the group consisting of methylcellulose, hydroxypropylmethylcellulose, hydroxybutylmethylcellulose, hydroxyethylmethylcellulose, ethylhydroxyethylcellulose, hydroxyethylcellulose, hydroxypropylcellulose, and mixtures thereof.

8. Pharmaceutical compositions for oral administration comprising:
    (a) from about 0.1% to about 50% of at least one pharmaceutically-acceptable bismuth-containing agent;
    (b) from about 0.1% to about 25% of methylcellulose; and
    (c) from about 0.1% to about 25% of magnesium aluminum silicate;
  and wherein further the ratio of bismuth to methylcellulose is greater than about 1.5:1.

9. Pharmaceutical compositions according to claim 8 comprising:
    (a) from about 1% to about 20% of at least one pharmaceutically-acceptable bismuth-containing agent selected from the group consisting of bismuth citrate, bismuth subcitrate, tripotassium dicitrato bismuthate, bismuth tartrate, bismuth subsalicylate, and mixtures thereof;

(b) from about 0.1% to about 10% of methylcellulose; and
(c) from about 0.1% to about 10% of magnesium aluminum silicate;

and wherein further the ratio of bismuth to methylcellulose is within the range of from about 1.5:1 to about 9:1.

10. Pharmaceutical compositions according to claim 9 in the form of a liquid comprising:
(a) from about 1% to about 5% of a pharmaceutically-acceptable bismuth-containing agent selected from the group consisting of bismuth subcitrate, bismuth subsalicylate, and mixtures thereof;
(b) from about 0.5% to about 3% of methylcellulose;
(c) from about 0.1% to about 5% of magnesium aluminum silicate; and
(d) from about 85% to about 98% of water;

and wherein further the ratio of bismuth to methylcellulose is within the range of from about 1.5:1 to about 3:1.

11. Pharmaceutical compositions for oral administration comprising:
(a) from about 0.1% to about 50% of bismuth subsalicylate;
(b) from about 0.1% to about 25% of methylcellulose; and
(c) from about 0.1% to about 25% of magnesium aluminum silicate;

and wherein further the ratio of bismuth to methylcellulose is greater than about 1.5:1.

12. Pharmaceutical compositions according to claim 11 comprising:
(a) from about 1% to about 20% of bismuth subsalicylate;
(b) from about 0.1% to about 10% of methylcellulose; and
(c) from about 0.1% to about 10% of magnesium aluminum silicate;

and wherein further the ratio of bismuth to methylcellulose is within the range of from about 1.5:1 to about 9:1.

13. Pharmaceutical compositions according to claim 12 comprising:
(a) from about 1% to about 5% of bismuth subsalicylate;
(b) from about 0.5% to about 3% of methylcellulose; and
(c) from about 0.1% to about 5% to magnesium aluminum silicate;

and wherein further the ratio of bismuth to methylcellulose is within the range of from about 1.5:1 to about 3:1.

14. Pharmaceutical compositions according to claim 13 in the form of a liquid further comprising from about 85% to about 98% of water.

15. Pharmaceutical compositions according to claim 14 comprising:
(a) from about 3% to about 4% of bismuth subsalicylate;
(b) from about 0.5% to about 1.5% of methylcellulose;
(c) from about 0.5% to about 1.5% of magnesium aluminum silicate; and
(d) from about 92% to about 96% of water;

and wherein further the ratio of bismuth to methylcellulose is within the range of from about 1.5:1 to about 2.5:1.

16. Pharmaceutical compositions according to claim 15 wherein further the ratio of bismuth to the total combined weight of methylcellulose and magnesium aluminum silicate is within the range of from about 0.5 to about 1.5:1.

17. Pharmaceutical compositions in liquid form for oral administration comprising:
(a) about 3.5% of bismuth subsalicylate;
(b) about 1% of methylcellulose;
(c) about 1% of magnesium alumimum silicate;
(d) about 94% of water; and
(e) one or more components selected from the group consisting of sweetening agents, preserving agents, coloring agents, flavoring agents, and mixtures thereof.

18. Methods for treating or preventing disturbances of the gastrointestinal tract in humans or lower animals, said methods comprising orally administering to a human or lower animal in need of such treatment or prevention, a safe and effective amount of a pharmaceutical composition according to claim 1.

19. Methods for treating or preventing disturbances of the gastrointestinal tract in humans or lower animals, said methods comprising orally administering to a human or lower animal in need of such treatment or prevention, a safe and effective amount of a pharmaceutical composition according to claim 4.

20. Methods for treating or preventing disturbances of the gastrointestinal tract in humans or lower animals, said methods comprising orally administering to a human or lower animal in need of such treatment or prevention, a safe and effective amount of a pharmaceutical composition according to claim 8.

21. Methods for treating or preventing disturbances of the gastrointestinal tract in humans or lower animals, said methods comprising orally administering to a human or lower animal in need of such treatment or prevention, a safe and effective amount of a pharmaceutical composition according to claim 11.

22. Methods for treating or preventing disturbances of the gastrointestinal tract in humans or lower animals, said methods comprising orally administering to a human or lower animal in need of such treatment or prevention, a safe and effective amount of a pharmaceutical composition according to claim 15.

23. Methods for treating or preventing disturbances of the gastrointestinal tract in humans or lower animals, said methods comprising orally administering to a human or lower animal in need of such treatment or prevention, a safe and effective amount of a pharmaceutical composition according to claim 17.

* * * * *